(12) United States Patent
Vainauskas et al.

(10) Patent No.: US 11,788,074 B2
(45) Date of Patent: Oct. 17, 2023

(54) VACCINIA CAPPING ENZYME COMPOSITIONS AND METHODS

(71) Applicant: New England Biolabs, Inc., Ipswich, MA (US)

(72) Inventors: Saulius Vainauskas, Newburyport, MA (US); Siu-Hong Chan, Ipswich, MA (US); Christopher H. Taron, Essex, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 17/348,127

(22) Filed: Jun. 15, 2021

(65) Prior Publication Data

US 2021/0395706 A1  Dec. 23, 2021

Related U.S. Application Data

(60) Provisional application No. 63/042,939, filed on Jun. 23, 2020.

(51) Int. Cl.
  *C12N 9/12* (2006.01)
  *C12N 15/81* (2006.01)
  *C12R 1/84* (2006.01)

(52) U.S. Cl.
  CPC ......... *C12N 9/1241* (2013.01); *C12N 15/815* (2013.01); *C07K 2319/00* (2013.01); *C12R 2001/84* (2021.05); *C12Y 207/0705* (2013.01)

(58) Field of Classification Search
  None
  See application file for complete search history.

(56) References Cited

U.S. PATENT DOCUMENTS

| | | | |
|---|---|---|---|
| 9,512,456 B2* | 12/2016 | Wang | C12N 9/1252 |
| 9,790,531 B2 | 10/2017 | Wang et al. | |
| 10,093,915 B2* | 10/2018 | Wu | C12Y 601/01021 |
| 2013/0042334 A1 | 2/2013 | Eukarys | |
| 2017/0253911 A1 | 9/2017 | Schildkraut et al. | |
| 2018/0237817 A1 | 8/2018 | Roos et al. | |

FOREIGN PATENT DOCUMENTS

WO  2019020811 A1  1/2019

OTHER PUBLICATIONS

Cong, et al (1993). "Covalent catalysis in nucleotidyl transfer. A KTDG motif essential for enzyme-GMP complex formation by mRNA capping enzyme is conserved at the active sites of RNA and DNA ligases." J Biol Chem 268(10):7256-60.
Niles, et al (1993). "Identification of the vaccinia virus mRNA guanyltransferase active site lysine." J Biol Chem 268(33): 24986-9.
Higman, et al (1994). "Location of the S-adenosyl-L-methionine binding region of the vaccinia virus mRNA (guanine-7-) methyltransferase." J Biol Chem 269(21): 14982-7.
Mao, et al (1994). "Intrinsic RNA (guanine-7) methyltransferase activity of the vaccinia virus capping enzyme D1 subunit is stimulated by the D12 subunit. Identification of amino acid residues in the D1 protein required for subunit association and methyl group transfer." J Biol Chem 269(39): 24472-9.
Gong, et al (2003). "Mapping the active site of vaccinia virus RNA triphosphatase." Virology 309(1): 125-34.
Higman, et al (1992). "The vaccinia virus mRNA (guanine-N-7-)-methyltransferase requires both subunits of the mRNA capping enzyme for activity." J Biol Chem 267(23): 16430-7.
Higman, et al (1994). "The mRNA (guanine-7) methyltransferase domain of the vaccinia virus mRNA capping enzyme. Expression in *Escherichia coli* and structural and kinetic comparison to the intact capping enzyme." J Biol Chem 269(21): 14974-81.
Osborn, et al., A picornaviral 2A-like sequence-based tricistronic vector allowing for high-level therapeutic gene expression coupled to a dual-reporter system. Mol Ther. 2005; 12:569-574.
Donnelly, et al Analysis of the aphthovirus 2A/2B polyprotein 'cleavage' mechanism indicates not a proteolytic reaction, but a novel translational effect: a putative ribosomal 'skip' J Gen Virol. 2001; 82:1013-1025.
Donnelly, et al., The 'cleavage' activities of foot-and-mouth disease virus 2A site-directed mutants and naturally occurring '2A-like' sequences. J Gen Virol. 2001; 82:1027-1041. doi: 10.1099/0022-1317-82-5-1027.
Lee, et al., Synergistic effects of 2A-mediated polyproteins on the production of lignocellulose degradation enzymes in tobacco plants. J Exp Bot. 2012; 63:4797-4810.
Rasala, et al. (2012). Robust expression and secretion of Xylanase1 in Chlamydomonas reinhardtii by fusion to a selection gene and processing with the FMDV 2A peptide. PLoS One. 7:e43349.
Chng, et al., (2015). Cleavage efficient 2A peptides for high level monoclonal antibody expression in CHO cells. MAbs. 7:403-412.
Sun, et al. (2012). Double Candida antarctica lipase B co-display on Pichia pastoris cell surface based on a self-processing foot-and-mouth disease virus 2A peptide. Appl Microbiol Biotechnol. 96:1539-1550.
De Amorim Araujo, et al., (2015). Coexpression of cellulases in Pichia pastoris as a self-processing protein fusion. AMB Express, 5(1), 84.
De Felipe, et al. (2003). Co-translational, intraribosomal cleavage of polypeptides by the foot-and-mouth disease virus 2A peptide. J Chem. 278:11441-11448.
Crasto, et al. (2000). Linker: a program to generate linker sequences for fusion proteins. Protein engineering, 13(5), 309-312.
Wu, et al. (2004). High efficiency transformation by electroporation of Pichia pastoris pretreated with lithium acetate and dithiothreitol. BioTechniques, 36(1), 152-154.

(Continued)

*Primary Examiner* — Richard G Hutson

(74) *Attorney, Agent, or Firm* — New England Biolabs, Inc

(57) ABSTRACT

The present disclosure relates, according to some embodiments, to compositions, methods, and/or kits for producing vaccinia capping enzyme. For example, active, heterodimers of vaccinia capping enzyme may be produced as fusions comprising D1 and D12 subunits. Vaccinia capping enzyme fusion proteins may further comprise a linker.

8 Claims, 4 Drawing Sheets

Specification includes a Sequence Listing.

(56) References Cited

OTHER PUBLICATIONS

Looke, et al.,(2011). Extraction of genomic DNA from yeasts for PCR-based applications. BioTechniques, 50(5), 325-328.
Ryan, et al., 1991, Cleavage of foot-and-mouth disease virus polyprotein is mediated by residues located within a 19 amino acid sequence. J Gen Virol. 72:2727-2732.
Benarroch, et al., Structure, 16, 501-512, 2008.
Shuman, The Journal of Biological Chemistry, 265, 20, 11960-11966, 1990.
Fuchs, et al., RNA, 22, 1454-1466, 2016.

* cited by examiner

SEQUENCE LISTING

<160> NUMBER OF SEQ ID NOS: 8

<210> SEQ ID NO 1
<211> LENGTH: 867
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<223> OTHER INFORMATION: D1 Polypeptide

<400> SEQUENCE: 1

```
Met Gly His His His His His His His His Ser Ser Gly His
1               5                   10                  15

Ile Glu Gly Arg His Arg Ser Met Asp Ala Asn Val Val Ser Ser
            20                  25                  30

Thr Ile Ala Thr Tyr Ile Asp Ala Leu Ala Lys Asn Ala Ser Glu Leu
        35                  40                  45

Glu Gln Arg Ser Thr Ala Tyr Glu Ile Asn Asn Glu Leu Glu Leu Val
    50                  55                  60

Phe Ile Lys Pro Pro Leu Ile Thr Leu Thr Asn Val Val Asn Ile Ser
65                  70                  75                  80

Thr Ile Gln Glu Ser Phe Ile Arg Phe Thr Val Thr Asn Lys Glu Gly
                85                  90                  95

Val Lys Ile Arg Thr Lys Ile Pro Leu Ser Lys Val His Gly Leu Asp
            100                 105                 110

Val Lys Asn Val Gln Leu Val Asp Ala Ile Asp Asn Ile Val Trp Glu
        115                 120                 125

Lys Lys Ser Leu Val Thr Glu Asn Arg Leu His Lys Glu Cys Leu Leu
    130                 135                 140

Arg Leu Ser Thr Glu Glu Arg His Ile Phe Leu Asp Tyr Lys Lys Tyr
145                 150                 155                 160

Gly Ser Ser Ile Arg Leu Glu Leu Val Asn Leu Ile Gln Ala Lys Thr
                165                 170                 175

Lys Asn Phe Thr Ile Asp Phe Lys Leu Lys Tyr Phe Leu Gly Ser Gly
            180                 185                 190

Ala Gln Ser Lys Ser Ser Leu Leu His Ala Ile Asn His Pro Lys Ser
        195                 200                 205

Arg Pro Asn Thr Ser Leu Glu Ile Glu Phe Thr Pro Arg Asp Asn Glu
    210                 215                 220

Thr Val Pro Tyr Asp Glu Leu Ile Lys Glu Leu Thr Thr Leu Ser Arg
225                 230                 235                 240

His Ile Phe Met Ala Ser Pro Glu Asn Val Ile Leu Ser Pro Pro Ile
                245                 250                 255

Asn Ala Pro Ile Lys Thr Phe Met Leu Pro Lys Gln Asp Ile Val Gly
            260                 265                 270

Leu Asp Leu Glu Asn Leu Tyr Ala Val Thr Lys Thr Asp Gly Ile Pro
        275                 280                 285

Ile Thr Ile Arg Val Thr Ser Asn Gly Leu Tyr Cys Tyr Phe Thr His
    290                 295                 300

Leu Gly Tyr Ile Ile Arg Tyr Pro Val Lys Arg Ile Ile Asp Ser Glu
305                 310                 315                 320

Val Val Val Phe Gly Glu Ala Val Lys Asp Lys Asn Trp Thr Val Tyr
                325                 330                 335
```

```
Leu Ile Lys Leu Ile Glu Pro Val Asn Ala Ile Asn Asp Arg Leu Glu
            340                 345                 350

Glu Ser Lys Tyr Val Glu Ser Lys Leu Val Asp Ile Cys Asp Arg Ile
            355                 360                 365

Val Phe Lys Ser Lys Tyr Glu Gly Pro Phe Thr Thr Thr Ser Glu
370                 375                 380

Val Val Asp Met Leu Ser Thr Tyr Leu Pro Lys Gln Pro Glu Gly Val
385                 390                 395                 400

Ile Leu Phe Tyr Ser Lys Gly Pro Lys Ser Asn Ile Asp Phe Lys Ile
            405                 410                 415

Lys Lys Glu Asn Thr Ile Asp Gln Thr Ala Asn Val Val Phe Arg Tyr
            420                 425                 430

Met Ser Ser Glu Pro Ile Ile Phe Gly Glu Ser Ser Ile Phe Val Glu
            435                 440                 445

Tyr Lys Lys Phe Ser Asn Asp Lys Gly Phe Pro Lys Glu Tyr Gly Ser
            450                 455                 460

Gly Lys Ile Val Leu Tyr Asn Gly Val Asn Tyr Leu Asn Asn Ile Tyr
465                 470                 475                 480

Cys Leu Glu Tyr Ile Asn Thr His Asn Glu Val Gly Ile Lys Ser Val
            485                 490                 495

Val Val Pro Ile Lys Phe Ile Ala Glu Phe Leu Val Asn Gly Glu Ile
            500                 505                 510

Leu Lys Pro Arg Ile Asp Lys Thr Met Lys Tyr Ile Asn Ser Glu Asp
            515                 520                 525

Tyr Tyr Gly Asn Gln His Asn Ile Ile Val Glu His Leu Arg Asp Gln
            530                 535                 540

Ser Ile Lys Ile Gly Asp Ile Phe Asn Glu Asp Lys Leu Ser Asp Val
545                 550                 555                 560

Gly His Gln Tyr Ala Asn Asn Asp Lys Phe Arg Leu Asn Pro Glu Val
            565                 570                 575

Ser Tyr Phe Thr Asn Lys Arg Thr Arg Gly Pro Leu Gly Ile Leu Ser
            580                 585                 590

Asn Tyr Val Lys Thr Leu Leu Ile Ser Met Tyr Cys Ser Lys Thr Phe
            595                 600                 605

Leu Asp Asp Ser Asn Lys Arg Lys Val Leu Ala Ile Asp Phe Gly Asn
            610                 615                 620

Gly Ala Asp Leu Glu Lys Tyr Phe Tyr Gly Glu Ile Ala Leu Leu Val
625                 630                 635                 640

Ala Thr Asp Pro Asp Ala Asp Ala Ile Ala Arg Gly Asn Glu Arg Tyr
            645                 650                 655

Asn Lys Leu Asn Ser Gly Ile Lys Thr Lys Tyr Tyr Lys Phe Asp Tyr
            660                 665                 670

Ile Gln Glu Thr Ile Arg Ser Asp Thr Phe Val Ser Ser Val Arg Glu
            675                 680                 685

Val Phe Tyr Phe Gly Lys Phe Asn Ile Ile Asp Trp Gln Phe Ala Ile
            690                 695                 700

His Tyr Ser Phe His Pro Arg His Tyr Ala Thr Val Met Asn Asn Leu
705                 710                 715                 720

Ser Glu Leu Thr Ala Ser Gly Gly Lys Val Leu Ile Thr Thr Met Asp
            725                 730                 735

Gly Asp Lys Leu Ser Lys Leu Thr Asp Lys Lys Thr Phe Ile Ile His
            740                 745                 750
```

```
Lys Asn Leu Pro Ser Ser Glu Asn Tyr Met Ser Val Glu Lys Ile Ala
            755                 760                 765

Asp Asp Arg Ile Val Val Tyr Asn Pro Ser Thr Met Ser Thr Pro Met
770                 775                 780

Thr Glu Tyr Ile Ile Lys Lys Asn Asp Ile Val Arg Val Phe Asn Glu
785                 790                 795                 800

Tyr Gly Phe Val Leu Val Asp Asn Val Asp Phe Ala Thr Ile Ile Glu
                805                 810                 815

Arg Ser Lys Lys Phe Ile Asn Gly Ala Ser Thr Met Glu Asp Arg Pro
            820                 825                 830

Ser Thr Arg Asn Phe Phe Glu Leu Asn Arg Gly Ala Ile Lys Cys Glu
            835                 840                 845

Gly Leu Asp Val Glu Asp Leu Leu Ser Tyr Tyr Val Val Tyr Val Phe
            850                 855                 860

Ser Lys Arg
865

<210> SEQ ID NO 2
<211> LENGTH: 287
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<223> OTHER INFORMATION: D12 polypeptide

<400> SEQUENCE: 2

Met Asp Glu Ile Val Lys Asn Ile Arg Glu Gly Thr His Val Leu Leu
1               5                   10                  15

Pro Phe Tyr Glu Thr Leu Pro Glu Leu Asn Leu Ser Leu Gly Lys Ser
            20                  25                  30

Pro Leu Pro Ser Leu Glu Tyr Gly Ala Asn Tyr Phe Leu Gln Ile Ser
        35                  40                  45

Arg Val Asn Asp Leu Asn Arg Met Pro Thr Asp Met Leu Lys Leu Phe
50                  55                  60

Thr His Asp Ile Met Leu Pro Ser Asp Leu Asp Lys Val Tyr Glu
65                  70                  75                  80

Ile Leu Lys Ile Asn Ser Val Lys Tyr Tyr Gly Arg Ser Thr Lys Ala
                85                  90                  95

Asp Ala Val Val Ala Asp Leu Ser Ala Arg Asn Lys Leu Phe Lys Arg
            100                 105                 110

Glu Arg Asp Ala Ile Lys Ser Asn Asn His Leu Thr Glu Asn Asn Leu
        115                 120                 125

Tyr Ile Ser Asp Tyr Lys Met Leu Thr Phe Asp Val Phe Arg Pro Leu
130                 135                 140

Phe Asp Phe Val Asn Glu Lys Tyr Cys Ile Ile Lys Leu Pro Thr Leu
145                 150                 155                 160

Phe Gly Arg Gly Val Ile Asp Thr Met Arg Ile Tyr Cys Ser Leu Phe
                165                 170                 175

Lys Asn Val Arg Leu Leu Lys Cys Val Ser Asp Ser Trp Leu Lys Asp
            180                 185                 190

Ser Ala Ile Met Val Ala Ser Asp Val Cys Lys Lys Asn Leu Asp Leu
        195                 200                 205

Phe Met Ser His Val Lys Ser Val Thr Lys Ser Ser Trp Lys Asp
210                 215                 220
```

-continued

Val Asn Ser Val Gln Phe Ser Ile Leu Asn Asn Pro Val Asp Thr Glu
225                 230                 235                 240

Phe Ile Asn Lys Phe Leu Glu Phe Ser Asn Arg Val Tyr Glu Ala Leu
            245                 250                 255

Tyr Tyr Val His Ser Leu Leu Tyr Ser Ser Met Thr Ser Asp Ser Lys
            260                 265                 270

Ser Ile Glu Asn Lys His Gln Arg Arg Leu Val Lys Leu Leu Leu
            275                 280                 285

<210> SEQ ID NO 3
<211> LENGTH: 33
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<223> OTHER INFORMATION: Linker 1D2A

<400> SEQUENCE: 3

Glu Ala Arg His Lys Gln Lys Ile Val Ala Pro Val Lys Gln Thr Leu
1               5                   10                  15

Asn Phe Asp Leu Leu Lys Leu Ala Gly Asp Val Glu Ser Asn Pro Gly
            20                  25                  30

Pro

<210> SEQ ID NO 4
<211> LENGTH: 1187
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<223> OTHER INFORMATION: D1-1D2A-D12 Polypeptide
<220> FEATURE:
<221> NAME/KEY: MISC_FEATURE
<222> LOCATION: (868)..(900)
<223> OTHER INFORMATION: 1D2A linker

<400> SEQUENCE: 4

Met Gly His His His His His His His His Ser Ser Gly His
1               5                   10                  15

Ile Glu Gly Arg His Arg Ser Met Asp Ala Asn Val Val Ser Ser Ser
            20                  25                  30

Thr Ile Ala Thr Tyr Ile Asp Ala Leu Ala Lys Asn Ala Ser Glu Leu
        35                  40                  45

Glu Gln Arg Ser Thr Ala Tyr Glu Ile Asn Asn Glu Leu Glu Leu Val
    50                  55                  60

Phe Ile Lys Pro Pro Leu Ile Thr Leu Thr Val Val Asn Ile Ser
65                  70                  75                  80

Thr Ile Gln Glu Ser Phe Ile Arg Phe Thr Val Thr Asn Lys Glu Gly
            85                  90                  95

Val Lys Ile Arg Thr Lys Ile Pro Leu Ser Lys Val His Gly Leu Asp
            100                 105                 110

Val Lys Asn Val Gln Leu Val Asp Ala Ile Asp Asn Ile Val Trp Glu
            115                 120                 125

Lys Lys Ser Leu Val Thr Glu Asn Arg Leu His Lys Glu Cys Leu Leu
    130                 135                 140

Arg Leu Ser Thr Glu Glu Arg His Ile Phe Leu Asp Tyr Lys Lys Tyr
145                 150                 155                 160

```
Gly Ser Ser Ile Arg Leu Glu Leu Val Asn Leu Ile Gln Ala Lys Thr
                165                 170                 175

Lys Asn Phe Thr Ile Asp Phe Lys Leu Lys Tyr Phe Leu Gly Ser Gly
            180                 185                 190

Ala Gln Ser Lys Ser Ser Leu Leu His Ala Ile Asn His Pro Lys Ser
        195                 200                 205

Arg Pro Asn Thr Ser Leu Glu Ile Glu Phe Thr Pro Arg Asp Asn Glu
    210                 215                 220

Thr Val Pro Tyr Asp Glu Leu Ile Lys Glu Leu Thr Thr Leu Ser Arg
225                 230                 235                 240

His Ile Phe Met Ala Ser Pro Glu Asn Val Ile Leu Ser Pro Pro Ile
                245                 250                 255

Asn Ala Pro Ile Lys Thr Phe Met Leu Pro Lys Gln Asp Ile Val Gly
            260                 265                 270

Leu Asp Leu Glu Asn Leu Tyr Ala Val Thr Lys Thr Asp Gly Ile Pro
        275                 280                 285

Ile Thr Ile Arg Val Thr Ser Asn Gly Leu Tyr Cys Tyr Phe Thr His
    290                 295                 300

Leu Gly Tyr Ile Ile Arg Tyr Pro Val Lys Arg Ile Ile Asp Ser Glu
305                 310                 315                 320

Val Val Val Phe Gly Glu Ala Val Lys Asp Lys Asn Trp Thr Val Tyr
                325                 330                 335

Leu Ile Lys Leu Ile Glu Pro Val Asn Ala Ile Asn Asp Arg Leu Glu
            340                 345                 350

Glu Ser Lys Tyr Val Glu Ser Lys Leu Val Asp Ile Cys Asp Arg Ile
        355                 360                 365

Val Phe Lys Ser Lys Lys Tyr Glu Gly Pro Phe Thr Thr Thr Ser Glu
    370                 375                 380

Val Val Asp Met Leu Ser Thr Tyr Leu Pro Lys Gln Pro Glu Gly Val
385                 390                 395                 400

Ile Leu Phe Tyr Ser Lys Gly Pro Lys Ser Asn Ile Asp Phe Lys Ile
                405                 410                 415

Lys Lys Glu Asn Thr Ile Asp Gln Thr Ala Asn Val Val Phe Arg Tyr
            420                 425                 430

Met Ser Ser Glu Pro Ile Ile Phe Gly Glu Ser Ser Ile Phe Val Glu
        435                 440                 445

Tyr Lys Lys Phe Ser Asn Asp Lys Gly Phe Pro Lys Glu Tyr Gly Ser
    450                 455                 460

Gly Lys Ile Val Leu Tyr Asn Gly Val Asn Tyr Leu Asn Asn Ile Tyr
465                 470                 475                 480

Cys Leu Glu Tyr Ile Asn Thr His Asn Glu Val Gly Ile Lys Ser Val
                485                 490                 495

Val Val Pro Ile Lys Phe Ile Ala Glu Phe Leu Val Asn Gly Glu Ile
            500                 505                 510

Leu Lys Pro Arg Ile Asp Lys Thr Met Lys Tyr Ile Asn Ser Glu Asp
        515                 520                 525

Tyr Tyr Gly Asn Gln His Asn Ile Ile Val Glu His Leu Arg Asp Gln
    530                 535                 540

Ser Ile Lys Ile Gly Asp Ile Phe Asn Glu Asp Lys Leu Ser Asp Val
545                 550                 555                 560

Gly His Gln Tyr Ala Asn Asn Asp Lys Phe Arg Leu Asn Pro Glu Val
                565                 570                 575
```

-continued

```
Ser Tyr Phe Thr Asn Lys Arg Thr Arg Gly Pro Leu Gly Ile Leu Ser
            580                 585                 590

Asn Tyr Val Lys Thr Leu Leu Ile Ser Met Tyr Cys Ser Lys Thr Phe
        595                 600                 605

Leu Asp Asp Ser Asn Lys Arg Lys Val Leu Ala Ile Asp Phe Gly Asn
    610                 615                 620

Gly Ala Asp Leu Glu Lys Tyr Phe Tyr Gly Glu Ile Ala Leu Leu Val
625                 630                 635                 640

Ala Thr Asp Pro Asp Ala Asp Ala Ile Ala Arg Gly Asn Glu Arg Tyr
                645                 650                 655

Asn Lys Leu Asn Ser Gly Ile Lys Thr Lys Tyr Tyr Lys Phe Asp Tyr
            660                 665                 670

Ile Gln Glu Thr Ile Arg Ser Asp Thr Phe Val Ser Ser Val Arg Glu
        675                 680                 685

Val Phe Tyr Phe Gly Lys Phe Asn Ile Ile Asp Trp Gln Phe Ala Ile
    690                 695                 700

His Tyr Ser Phe His Pro Arg His Tyr Ala Thr Val Met Asn Asn Leu
705                 710                 715                 720

Ser Glu Leu Thr Ala Ser Gly Gly Lys Val Leu Ile Thr Thr Met Asp
                725                 730                 735

Gly Asp Lys Leu Ser Lys Leu Thr Asp Lys Lys Thr Phe Ile Ile His
            740                 745                 750

Lys Asn Leu Pro Ser Ser Glu Asn Tyr Met Ser Val Glu Lys Ile Ala
        755                 760                 765

Asp Asp Arg Ile Val Val Tyr Asn Pro Ser Thr Met Ser Thr Pro Met
    770                 775                 780

Thr Glu Tyr Ile Ile Lys Lys Asn Asp Ile Val Arg Val Phe Asn Glu
785                 790                 795                 800

Tyr Gly Phe Val Leu Val Asp Asn Val Asp Phe Ala Thr Ile Ile Glu
                805                 810                 815

Arg Ser Lys Lys Phe Ile Asn Gly Ala Ser Thr Met Glu Asp Arg Pro
            820                 825                 830

Ser Thr Arg Asn Phe Phe Glu Leu Asn Arg Gly Ala Ile Lys Cys Glu
        835                 840                 845

Gly Leu Asp Val Glu Asp Leu Leu Ser Tyr Tyr Val Val Tyr Val Phe
    850                 855                 860

Ser Lys Arg Glu Ala Arg His Lys Gln Lys Ile Val Ala Pro Val Lys
865                 870                 875                 880

Gln Thr Leu Asn Phe Asp Leu Leu Lys Leu Ala Gly Asp Val Glu Ser
                885                 890                 895

Asn Pro Gly Pro Met Asp Glu Ile Val Lys Asn Ile Arg Glu Gly Thr
            900                 905                 910

His Val Leu Leu Pro Phe Tyr Glu Thr Leu Pro Glu Leu Asn Leu Ser
        915                 920                 925

Leu Gly Lys Ser Pro Leu Pro Ser Leu Glu Tyr Gly Ala Asn Tyr Phe
    930                 935                 940

Leu Gln Ile Ser Arg Val Asn Asp Leu Asn Arg Met Pro Thr Asp Met
945                 950                 955                 960

Leu Lys Leu Phe Thr His Asp Ile Met Leu Pro Glu Ser Asp Leu Asp
                965                 970                 975

Lys Val Tyr Glu Ile Leu Lys Ile Asn Ser Val Lys Tyr Tyr Gly Arg
            980                 985                 990
```

```
Ser Thr Lys Ala Asp Ala Val Val  Ala Asp Leu Ser Ala  Arg Asn Lys
        995              1000                1005

Leu Phe  Lys Arg Glu Arg  Asp Ala Ile Lys Ser Asn  Asn His Leu
    1010             1015                1020

Thr Glu  Asn Asn Leu Tyr Ile  Ser Asp Tyr Lys Met  Leu Thr Phe
    1025             1030                1035

Asp Val  Phe Arg Pro Leu Phe  Asp Phe Val Asn Glu  Lys Tyr Cys
    1040             1045                1050

Ile Ile  Lys Leu Pro Thr Leu  Phe Gly Arg Gly Val  Ile Asp Thr
    1055             1060                1065

Met Arg  Ile Tyr Cys Ser Leu  Phe Lys Asn Val Arg  Leu Leu Lys
    1070             1075                1080

Cys Val  Ser Asp Ser Trp Leu  Lys Asp Ser Ala Ile  Met Val Ala
    1085             1090                1095

Ser Asp  Val Cys Lys Lys Asn  Leu Asp Leu Phe Met  Ser His Val
    1100             1105                1110

Lys Ser  Val Thr Lys Ser Ser  Ser Trp Lys Asp Val  Asn Ser Val
    1115             1120                1125

Gln Phe  Ser Ile Leu Asn Asn  Pro Val Asp Thr Glu  Phe Ile Asn
    1130             1135                1140

Lys Phe  Leu Glu Phe Ser Asn  Arg Val Tyr Glu Ala  Leu Tyr Tyr
    1145             1150                1155

Val His  Ser Leu Leu Tyr Ser  Ser Met Thr Ser Asp  Ser Lys Ser
    1160             1165                1170

Ile Glu  Asn Lys His Gln Arg  Arg Leu Val Lys Leu  Leu Leu
    1175             1180                1185

<210> SEQ ID NO 5
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<223> OTHER INFORMATION: Flexible Linker GS

<400> SEQUENCE: 5

Gly Gly Gly Gly Ser Gly Gly Gly Ser Gly Gly Gly Gly Ser
1               5                   10                  15

<210> SEQ ID NO 6
<211> LENGTH: 1169
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<223> OTHER INFORMATION: D1-GS-D12 Polypeptide

<400> SEQUENCE: 6

Met Gly His His His His His His His His Ser Ser Gly His
1               5                   10                  15

Ile Glu Gly Arg His Arg Ser Met Asp Ala Asn Val Val Ser Ser
                20                  25                  30

Thr Ile Ala Thr Tyr Ile Asp Ala Leu Ala Lys Asn Ala Ser Glu Leu
            35                  40                  45
```

```
Glu Gln Arg Ser Thr Ala Tyr Glu Ile Asn Asn Glu Leu Glu Leu Val
    50                  55                  60

Phe Ile Lys Pro Pro Leu Ile Thr Leu Thr Asn Val Val Asn Ile Ser
65                  70                  75                  80

Thr Ile Gln Glu Ser Phe Ile Arg Phe Thr Val Thr Asn Lys Glu Gly
                85                  90                  95

Val Lys Ile Arg Thr Lys Ile Pro Leu Ser Lys Val His Gly Leu Asp
            100                 105                 110

Val Lys Asn Val Gln Leu Val Asp Ala Ile Asp Asn Ile Val Trp Glu
        115                 120                 125

Lys Lys Ser Leu Val Thr Glu Asn Arg Leu His Lys Glu Cys Leu Leu
    130                 135                 140

Arg Leu Ser Thr Glu Glu Arg His Ile Phe Leu Asp Tyr Lys Lys Tyr
145                 150                 155                 160

Gly Ser Ser Ile Arg Leu Glu Leu Val Asn Leu Ile Gln Ala Lys Thr
                165                 170                 175

Lys Asn Phe Thr Ile Asp Phe Lys Leu Lys Tyr Phe Leu Gly Ser Gly
            180                 185                 190

Ala Gln Ser Lys Ser Ser Leu Leu His Ala Ile Asn His Pro Lys Ser
        195                 200                 205

Arg Pro Asn Thr Ser Leu Glu Ile Glu Phe Thr Pro Arg Asp Asn Glu
210                 215                 220

Thr Val Pro Tyr Asp Glu Leu Ile Lys Glu Leu Thr Thr Leu Ser Arg
225                 230                 235                 240

His Ile Phe Met Ala Ser Pro Glu Asn Val Ile Leu Ser Pro Pro Ile
                245                 250                 255

Asn Ala Pro Ile Lys Thr Phe Met Leu Pro Lys Gln Asp Ile Val Gly
            260                 265                 270

Leu Asp Leu Glu Asn Leu Tyr Ala Val Thr Lys Thr Asp Gly Ile Pro
        275                 280                 285

Ile Thr Ile Arg Val Thr Ser Asn Gly Leu Tyr Cys Tyr Phe Thr His
        290                 295                 300

Leu Gly Tyr Ile Ile Arg Tyr Pro Val Lys Arg Ile Ile Asp Ser Glu
305                 310                 315                 320

Val Val Val Phe Gly Glu Ala Val Lys Asp Lys Asn Trp Thr Val Tyr
                325                 330                 335

Leu Ile Lys Leu Ile Glu Pro Val Asn Ala Ile Asn Asp Arg Leu Glu
            340                 345                 350

Glu Ser Lys Tyr Val Glu Ser Lys Leu Val Asp Ile Cys Asp Arg Ile
        355                 360                 365

Val Phe Lys Ser Lys Lys Tyr Glu Gly Pro Phe Thr Thr Thr Ser Glu
    370                 375                 380

Val Val Asp Met Leu Ser Thr Tyr Leu Pro Lys Gln Pro Glu Gly Val
385                 390                 395                 400

Ile Leu Phe Tyr Ser Lys Gly Pro Lys Ser Asn Ile Asp Phe Lys Ile
                405                 410                 415

Lys Lys Glu Asn Thr Ile Asp Gln Thr Ala Asn Val Val Phe Arg Tyr
            420                 425                 430

Met Ser Ser Glu Pro Ile Ile Phe Gly Glu Ser Ser Ile Phe Val Glu
        435                 440                 445

Tyr Lys Lys Phe Ser Asn Asp Lys Gly Phe Pro Lys Glu Tyr Gly Ser
    450                 455                 460
```

```
Gly Lys Ile Val Leu Tyr Asn Gly Val Asn Tyr Leu Asn Asn Ile Tyr
465                 470                 475                 480

Cys Leu Glu Tyr Ile Asn Thr His Asn Glu Val Gly Ile Lys Ser Val
                485                 490                 495

Val Val Pro Ile Lys Phe Ile Ala Glu Phe Leu Val Asn Gly Glu Ile
            500                 505                 510

Leu Lys Pro Arg Ile Asp Lys Thr Met Lys Tyr Ile Asn Ser Glu Asp
            515                 520                 525

Tyr Tyr Gly Asn Gln His Asn Ile Ile Val Glu His Leu Arg Asp Gln
        530                 535                 540

Ser Ile Lys Ile Gly Asp Ile Phe Asn Glu Asp Lys Leu Ser Asp Val
545                 550                 555                 560

Gly His Gln Tyr Ala Asn Asn Asp Lys Phe Arg Leu Asn Pro Glu Val
                565                 570                 575

Ser Tyr Phe Thr Asn Lys Arg Thr Arg Gly Pro Leu Gly Ile Leu Ser
            580                 585                 590

Asn Tyr Val Lys Thr Leu Leu Ile Ser Met Tyr Cys Ser Lys Thr Phe
        595                 600                 605

Leu Asp Asp Ser Asn Lys Arg Lys Val Leu Ala Ile Asp Phe Gly Asn
610                 615                 620

Gly Ala Asp Leu Glu Lys Tyr Phe Tyr Gly Glu Ile Ala Leu Leu Val
625                 630                 635                 640

Ala Thr Asp Pro Asp Ala Asp Ala Ile Ala Arg Gly Asn Glu Arg Tyr
                645                 650                 655

Asn Lys Leu Asn Ser Gly Ile Lys Thr Lys Tyr Tyr Lys Phe Asp Tyr
            660                 665                 670

Ile Gln Glu Thr Ile Arg Ser Asp Thr Phe Val Ser Ser Val Arg Glu
        675                 680                 685

Val Phe Tyr Phe Gly Lys Phe Asn Ile Ile Asp Trp Gln Phe Ala Ile
        690                 695                 700

His Tyr Ser Phe His Pro Arg His Tyr Ala Thr Val Met Asn Asn Leu
705                 710                 715                 720

Ser Glu Leu Thr Ala Ser Gly Gly Lys Val Leu Ile Thr Thr Met Asp
                725                 730                 735

Gly Asp Lys Leu Ser Lys Leu Thr Asp Lys Lys Thr Phe Ile Ile His
            740                 745                 750

Lys Asn Leu Pro Ser Ser Glu Asn Tyr Met Ser Val Glu Lys Ile Ala
        755                 760                 765

Asp Asp Arg Ile Val Val Tyr Asn Pro Ser Thr Met Ser Thr Pro Met
770                 775                 780

Thr Glu Tyr Ile Ile Lys Lys Asn Asp Ile Val Arg Val Phe Asn Glu
785                 790                 795                 800

Tyr Gly Phe Val Leu Val Asp Asn Val Asp Phe Ala Thr Ile Ile Glu
                805                 810                 815

Arg Ser Lys Lys Phe Ile Asn Gly Ala Ser Thr Met Glu Asp Arg Pro
            820                 825                 830

Ser Thr Arg Asn Phe Phe Glu Leu Asn Arg Gly Ala Ile Lys Cys Glu
        835                 840                 845

Gly Leu Asp Val Glu Asp Leu Leu Ser Tyr Tyr Val Val Tyr Val Phe
850                 855                 860

Ser Lys Arg Gly Gly Gly Ser Gly Gly Gly Ser Gly Gly Gly
865                 870                 875                 880
```

```
Gly Ser Met Asp Glu Ile Val Lys Asn Ile Arg Gly Thr His Val
                885                 890                 895

Leu Leu Pro Phe Tyr Glu Thr Leu Pro Glu Leu Asn Leu Ser Leu Gly
        900                 905                 910

Lys Ser Pro Leu Pro Ser Leu Glu Tyr Gly Ala Asn Tyr Phe Leu Gln
        915                 920                 925

Ile Ser Arg Val Asn Asp Leu Asn Arg Met Pro Thr Asp Met Leu Lys
        930                 935                 940

Leu Phe Thr His Asp Ile Met Leu Pro Glu Ser Asp Leu Asp Lys Val
945                 950                 955                 960

Tyr Glu Ile Leu Lys Ile Asn Ser Val Lys Tyr Gly Arg Ser Thr
                965                 970                 975

Lys Ala Asp Ala Val Val Ala Asp Leu Ser Ala Arg Asn Lys Leu Phe
        980                 985                 990

Lys Arg Glu Arg Asp Ala Ile Lys  Ser Asn Asn His Leu  Thr Glu Asn
        995                 1000                1005

Asn Leu  Tyr Ile Ser Asp Tyr  Lys Met Leu Thr Phe  Asp Val Phe
    1010                 1015                 1020

Arg Pro  Leu Phe Asp Phe Val  Asn Glu Lys Tyr Cys  Ile Ile Lys
    1025                 1030                 1035

Leu Pro  Thr Leu Phe Gly Arg  Gly Val Ile Asp Thr  Met Arg Ile
    1040                 1045                 1050

Tyr Cys  Ser Leu Phe Lys Asn  Val Arg Leu Leu Lys  Cys Val Ser
    1055                 1060                 1065

Asp Ser  Trp Leu Lys Asp Ser  Ala Ile Met Val Ala  Ser Asp Val
    1070                 1075                 1080

Cys Lys  Lys Asn Leu Asp Leu  Phe Met Ser His Val  Lys Ser Val
    1085                 1090                 1095

Thr Lys  Ser Ser Ser Trp Lys  Asp Val Asn Ser Val  Gln Phe Ser
    1100                 1105                 1110

Ile Leu  Asn Asn Pro Val Asp  Thr Glu Phe Ile Asn  Lys Phe Leu
    1115                 1120                 1125

Glu Phe  Ser Asn Arg Val Tyr  Glu Ala Leu Tyr Tyr  Val His Ser
    1130                 1135                 1140

Leu Leu  Tyr Ser Ser Met Thr  Ser Asp Ser Lys Ser  Ile Glu Asn
    1145                 1150                 1155

Lys His  Gln Arg Arg Leu Val  Lys Leu Leu Leu
    1160                 1165

<210> SEQ ID NO 7
<211> LENGTH: 25
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Substrate RNA
<220> FEATURE:
<221> NAME/KEY: misc_feature
<223> OTHER INFORMATION: 3' FAM
<220> FEATURE:
<221> NAME/KEY: modified_base
<222> LOCATION: (1)..(1)
<223> OTHER INFORMATION: 5' triphosphate

<400> SEQUENCE: 7
guagaacuuc gucgaguacg cucaa                                       25
```

<210> SEQ ID NO 8
<211> LENGTH: 1132
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<223> OTHER INFORMATION: D1-Linker-D12 Polypeptide
<220> FEATURE:
<221> NAME/KEY: MISC_FEATURE
<222> LOCATION: (845)..(845)
<223> OTHER INFORMATION: Xaa is a peptide linker from 2-100 residues in
      length, wherein each position is independently any amino acid

<400> SEQUENCE: 8

```
Met Asp Ala Asn Val Val Ser Ser Thr Ile Ala Thr Tyr Ile Asp
1               5                   10                  15

Ala Leu Ala Lys Asn Ala Ser Glu Leu Glu Gln Arg Ser Thr Ala Tyr
                20                  25                  30

Glu Ile Asn Asn Glu Leu Glu Leu Val Phe Ile Lys Pro Pro Leu Ile
            35                  40                  45

Thr Leu Thr Asn Val Val Asn Ile Ser Thr Ile Gln Glu Ser Phe Ile
50                  55                  60

Arg Phe Thr Val Thr Asn Lys Glu Gly Val Lys Ile Arg Thr Lys Ile
65                  70                  75                  80

Pro Leu Ser Lys Val His Gly Leu Asp Val Lys Asn Val Gln Leu Val
                85                  90                  95

Asp Ala Ile Asp Asn Ile Val Trp Glu Lys Lys Ser Leu Val Thr Glu
            100                 105                 110

Asn Arg Leu His Lys Glu Cys Leu Leu Arg Leu Ser Thr Glu Glu Arg
        115                 120                 125

His Ile Phe Leu Asp Tyr Lys Lys Tyr Gly Ser Ser Ile Arg Leu Glu
    130                 135                 140

Leu Val Asn Leu Ile Gln Ala Lys Thr Lys Asn Phe Thr Ile Asp Phe
145                 150                 155                 160

Lys Leu Lys Tyr Phe Leu Gly Ser Gly Ala Gln Ser Lys Ser Ser Leu
                165                 170                 175

Leu His Ala Ile Asn His Pro Lys Ser Arg Pro Asn Thr Ser Leu Glu
            180                 185                 190

Ile Glu Phe Thr Pro Arg Asp Asn Glu Thr Val Pro Tyr Asp Glu Leu
        195                 200                 205

Ile Lys Glu Leu Thr Thr Leu Ser Arg His Ile Phe Met Ala Ser Pro
    210                 215                 220

Glu Asn Val Ile Leu Ser Pro Pro Ile Asn Ala Pro Ile Lys Thr Phe
225                 230                 235                 240

Met Leu Pro Lys Gln Asp Ile Val Gly Leu Asp Leu Glu Asn Leu Tyr
                245                 250                 255

Ala Val Thr Lys Thr Asp Gly Ile Pro Ile Thr Ile Arg Val Thr Ser
            260                 265                 270

Asn Gly Leu Tyr Cys Tyr Phe Thr His Leu Gly Tyr Ile Ile Arg Tyr
        275                 280                 285

Pro Val Lys Arg Ile Ile Asp Ser Glu Val Val Val Phe Gly Glu Ala
    290                 295                 300

Val Lys Asp Lys Asn Trp Thr Val Tyr Leu Ile Lys Leu Ile Glu Pro
305                 310                 315                 320
```

```
Val Asn Ala Ile Asn Asp Arg Leu Glu Glu Ser Lys Tyr Val Glu Ser
            325                 330                 335

Lys Leu Val Asp Ile Cys Asp Arg Ile Val Phe Lys Ser Lys Lys Tyr
            340                 345                 350

Glu Gly Pro Phe Thr Thr Thr Ser Glu Val Val Asp Met Leu Ser Thr
            355                 360                 365

Tyr Leu Pro Lys Gln Pro Glu Gly Val Ile Leu Phe Tyr Ser Lys Gly
            370                 375             380

Pro Lys Ser Asn Ile Asp Phe Lys Ile Lys Lys Glu Asn Thr Ile Asp
385                 390                 395                 400

Gln Thr Ala Asn Val Val Phe Arg Tyr Met Ser Ser Glu Pro Ile Ile
                405                 410                 415

Phe Gly Glu Ser Ser Ile Phe Val Glu Tyr Lys Lys Phe Ser Asn Asp
                420                 425             430

Lys Gly Phe Pro Lys Glu Tyr Gly Ser Gly Lys Ile Val Leu Tyr Asn
            435                 440                 445

Gly Val Asn Tyr Leu Asn Asn Ile Tyr Cys Leu Glu Tyr Ile Asn Thr
    450                 455                 460

His Asn Glu Val Gly Ile Lys Ser Val Val Pro Ile Lys Phe Ile
465                 470                 475                 480

Ala Glu Phe Leu Val Asn Gly Glu Ile Leu Lys Pro Arg Ile Asp Lys
                485                 490                 495

Thr Met Lys Tyr Ile Asn Ser Glu Asp Tyr Tyr Gly Asn Gln His Asn
                500                 505             510

Ile Ile Val Glu His Leu Arg Asp Gln Ser Ile Lys Ile Gly Asp Ile
            515                 520                 525

Phe Asn Glu Asp Lys Leu Ser Asp Val Gly His Gln Tyr Ala Asn Asn
            530                 535             540

Asp Lys Phe Arg Leu Asn Pro Glu Val Ser Tyr Phe Thr Asn Lys Arg
545                 550                 555             560

Thr Arg Gly Pro Leu Gly Ile Leu Ser Asn Tyr Val Lys Thr Leu Leu
            565                 570                 575

Ile Ser Met Tyr Cys Ser Lys Thr Phe Leu Asp Asp Ser Asn Lys Arg
            580                 585             590

Lys Val Leu Ala Ile Asp Phe Gly Asn Gly Ala Asp Leu Glu Lys Tyr
            595                 600             605

Phe Tyr Gly Glu Ile Ala Leu Leu Val Ala Thr Asp Pro Asp Ala Asp
            610                 615                 620

Ala Ile Ala Arg Gly Asn Glu Arg Tyr Asn Lys Leu Asn Ser Gly Ile
625                 630                 635             640

Lys Thr Lys Tyr Tyr Lys Phe Asp Tyr Ile Gln Glu Thr Ile Arg Ser
                645                 650             655

Asp Thr Phe Val Ser Ser Val Arg Glu Val Phe Tyr Phe Gly Lys Phe
            660                 665                 670

Asn Ile Ile Asp Trp Gln Phe Ala Ile His Tyr Ser Phe His Pro Arg
            675                 680             685

His Tyr Ala Thr Val Met Asn Asn Leu Ser Glu Leu Thr Ala Ser Gly
            690                 695             700

Gly Lys Val Leu Ile Thr Thr Met Asp Gly Asp Lys Leu Ser Lys Leu
705                 710                 715             720

Thr Asp Lys Lys Thr Phe Ile Ile His Lys Asn Leu Pro Ser Ser Glu
                725                 730                 735
```

```
Asn Tyr Met Ser Val Glu Lys Ile Ala Asp Asp Arg Ile Val Val Tyr
            740                 745                 750

Asn Pro Ser Thr Met Ser Thr Pro Met Thr Glu Tyr Ile Ile Lys Lys
            755                 760                 765

Asn Asp Ile Val Arg Val Phe Asn Glu Tyr Gly Phe Val Leu Val Asp
            770                 775                 780

Asn Val Asp Phe Ala Thr Ile Ile Glu Arg Ser Lys Lys Phe Ile Asn
785                 790                 795                 800

Gly Ala Ser Thr Met Glu Asp Arg Pro Ser Thr Arg Asn Phe Phe Glu
                805                 810                 815

Leu Asn Arg Gly Ala Ile Lys Cys Glu Gly Leu Asp Val Glu Asp Leu
            820                 825                 830

Leu Ser Tyr Tyr Val Val Tyr Val Phe Ser Lys Arg Xaa Met Asp Glu
            835                 840                 845

Ile Val Lys Asn Ile Arg Glu Gly Thr His Val Leu Leu Pro Phe Tyr
            850                 855                 860

Glu Thr Leu Pro Glu Leu Asn Leu Ser Leu Gly Lys Ser Pro Leu Pro
865                 870                 875                 880

Ser Leu Glu Tyr Gly Ala Asn Tyr Phe Leu Gln Ile Ser Arg Val Asn
                885                 890                 895

Asp Leu Asn Arg Met Pro Thr Asp Met Leu Lys Leu Phe Thr His Asp
            900                 905                 910

Ile Met Leu Pro Glu Ser Asp Leu Asp Lys Val Tyr Glu Ile Leu Lys
            915                 920                 925

Ile Asn Ser Val Lys Tyr Tyr Gly Arg Ser Thr Lys Ala Asp Ala Val
            930                 935                 940

Val Ala Asp Leu Ser Ala Arg Asn Lys Leu Phe Lys Arg Glu Arg Asp
945                 950                 955                 960

Ala Ile Lys Ser Asn Asn His Leu Thr Glu Asn Asn Leu Tyr Ile Ser
                965                 970                 975

Asp Tyr Lys Met Leu Thr Phe Asp Val Phe Arg Pro Leu Phe Asp Phe
            980                 985                 990

Val Asn Glu Lys Tyr Cys Ile Ile Lys Leu Pro Thr Leu Phe Gly Arg
            995                 1000                1005

Gly Val Ile Asp Thr Met Arg Ile Tyr Cys Ser Leu Phe Lys Asn
            1010                1015                1020

Val Arg Leu Leu Lys Cys Val Ser Asp Ser Trp Leu Lys Asp Ser
            1025                1030                1035

Ala Ile Met Val Ala Ser Asp Val Cys Lys Lys Asn Leu Asp Leu
            1040                1045                1050

Phe Met Ser His Val Lys Ser Val Thr Lys Ser Ser Trp Lys
            1055                1060                1065

Asp Val Asn Ser Val Gln Phe Ser Ile Leu Asn Asn Pro Val Asp
            1070                1075                1080

Thr Glu Phe Ile Asn Lys Phe Leu Glu Phe Ser Asn Arg Val Tyr
            1085                1090                1095

Glu Ala Leu Tyr Tyr Val His Ser Leu Leu Tyr Ser Ser Met Thr
            1100                1105                1110

Ser Asp Ser Lys Ser Ile Glu Asn Lys His Gln Arg Arg Leu Val
            1115                1120                1125

Lys Leu Leu Leu
    1130
```

US 11,788,074 B2

1

VACCINIA CAPPING ENZYME COMPOSITIONS AND METHODS

CROSS-REFERENCE TO RELATED APPLICATIONS

This application claims priority to U.S. Provisional Application No. 63/042,939 filed Jun. 23, 2020, the entire contents of which are hereby incorporated by reference.

BACKGROUND

The vaccinia RNA capping enzyme is a heterodimer consisting of a 97 kDa subunit encoded by the vaccinia virus D1R gene (GeneID:3707562; UniProtKB ID: YP 232988.1) and a 33-kDa subunit encoded by the vaccinia virus D12L gene (GeneID:3707515; UniProtKB ID: YP 232999.1). D1 is a catalytic subunit, which has RNA-triphosphatase, RNA guanylyltransferase and RNA N7-guanine methyltransferase enzymatic activities (Cong and Shuman 1993; Niles and Christen 1993; Higman and Niles 1994; Mao and Shuman 1994; Gong and Shuman 2003), whereas regulatory D12 subunit itself has no known enzymatic activity, but stimulates significantly the RNA N7-guanine methyltransferase activity of the D1 subunit (Higman, Bourgeois et al. 1992; Higman, Christen et al. 1994; Mao and Shuman 1994).

SUMMARY

The present disclosure relates to compositions, methods, and/or kits for producing vaccinia capping enzyme. For example, a vaccinia capping enzyme fusion transcript (e.g., a polynucleotide template for a fusion protein) may comprise, in a 5' to 3' direction: (a) a sequence encoding a D1 subunit, (b) a linker (e.g., an 1D2A linker, a sequence encoding a flexible linker or a cleavable linker), and (c) a sequence encoding a D12 subunit. The present disclosure further relates to compositions comprising a vaccinia capping enzyme fusion transcript. A D1 subunit encoded by a vaccinia capping enzyme fusion transcript may have an amino acid sequence having at least 90% identity to positions 24 to 867 of SEQ ID NO: 1 and/or may have an amino acid sequence having at least 90% identity to SEQ ID NO: 1. A linker may have an amino acid sequence having at least 90% identity to SEQ ID NO: 3 or an amino acid sequence having at least 90% identity to SEQ ID NO: 5. A D12 subunit encoded by a vaccinia capping enzyme fusion transcript may have an amino acid sequence having at least 90% identity to SEQ ID NO: 2. A vaccinia capping enzyme fusion transcript may comprise a cap and/or a polyA tail. In some embodiments, a vaccinia capping enzyme fusion transcript may be introduced or otherwise present (e.g., transcribed from an expression cassette) in a cell. A cell having a vaccinia capping enzyme fusion transcript may comprise equimolar amounts of D1 and D12. A cell may comprise a catalytically active vaccinia capping enzyme. A vaccinia capping enzyme fusion protein in a cell may have an amino acid sequence at least 90% identical to SEQ ID NO: 4 or at least 90% identical to SEQ ID NO: 6 or at least 90% identical to SEQ ID NO: 8.

The present disclosure related to vaccinia capping enzyme fusions and compositions comprising such fusion proteins. For example, a vaccinia capping enzyme fusion enzyme (e.g., included in a composition) may comprise, in an N-terminal to C-terminal orientation, a D1 subunit, a linker,

2 and a D12 subunit. The present disclosure further provides expressible polynucleotides (e.g., DNA) encoding vaccinia capping enzyme fusions.

A D1 subunit of a vaccinia capping enzyme fusion may have an amino acid sequence having at least 90% identity to positions 24 to 867 of SEQ ID NO: 1 and/or may have an amino acid sequence having at least 90% identity to SEQ ID NO: 1. A linker of a vaccinia capping enzyme fusion may have an amino acid sequence having at least 90% identity to SEQ ID NO: 3 or an amino acid sequence having at least 90% identity to SEQ ID NO: 5. A D12 subunit of a vaccinia capping enzyme fusion may have an amino acid sequence having at least 90% identity to SEQ ID NO: 2.

In some embodiments, methods of producing a vaccinia capping enzyme (e.g., a catalytically active vaccinia capping enzyme) may comprise contacting a vaccinia capping enzyme fusion transcript with a suitable expression system. A vaccinia capping enzyme fusion transcript may comprise, in a 5' to 3' orientation, (i) a sequence encoding D1, (ii) a sequence encoding a linker, and (iii) a sequence encoding D12. In some embodiments, an expression system may be a yeast expression system comprising, for example, *Kluyveromyces lactis* or *Pichia pastoris*. A vaccinia capping enzyme fusion transcript may comprise a cap and/or a polyA tail. Producing a vaccinia capping enzyme may comprise contacting a bacteria or a yeast comprising a DNA encoding a vaccinia capping enzyme fusion or fusion transcript operably linked to an expression control sequence with suitable media under conditions and for a time sufficient to permit such bacteria or yeast to produce the vaccinia capping enzyme fusion transcript and/or the vaccinia capping enzyme fusion encoded by the vaccinia capping enzyme fusion transcript. The produced vaccinia capping enzyme may comprise equimolar quantities of D1 and D12.

A kit for capping a transcript, according to some embodiments, may comprise a composition comprising a vaccinia capping enzyme fusion and, optionally, a mastermix. A kit may further comprise one or more additional enzymes including, for example, a decapping enzyme. A kit for producing a vaccinia capping enzyme fusion may comprise (a) a vaccinia capping enzyme fusion transcript comprising, in a 5' to 3' orientation, (i) a sequence encoding D1, (ii) a sequence encoding a linker, and (iii) a sequence encoding D12 and (b) an expression system (e.g., a cell-free, a bacterial, or a yeast expression system).

BRIEF DESCRIPTION OF THE FIGURES

The file of this patent contains at least one drawing executed in color. Copies of this patent with color drawing(s) will be provided by the Patent and Trademark Office upon request and payment of the necessary fee.

DETAILED DESCRIPTION

Figure 1A:
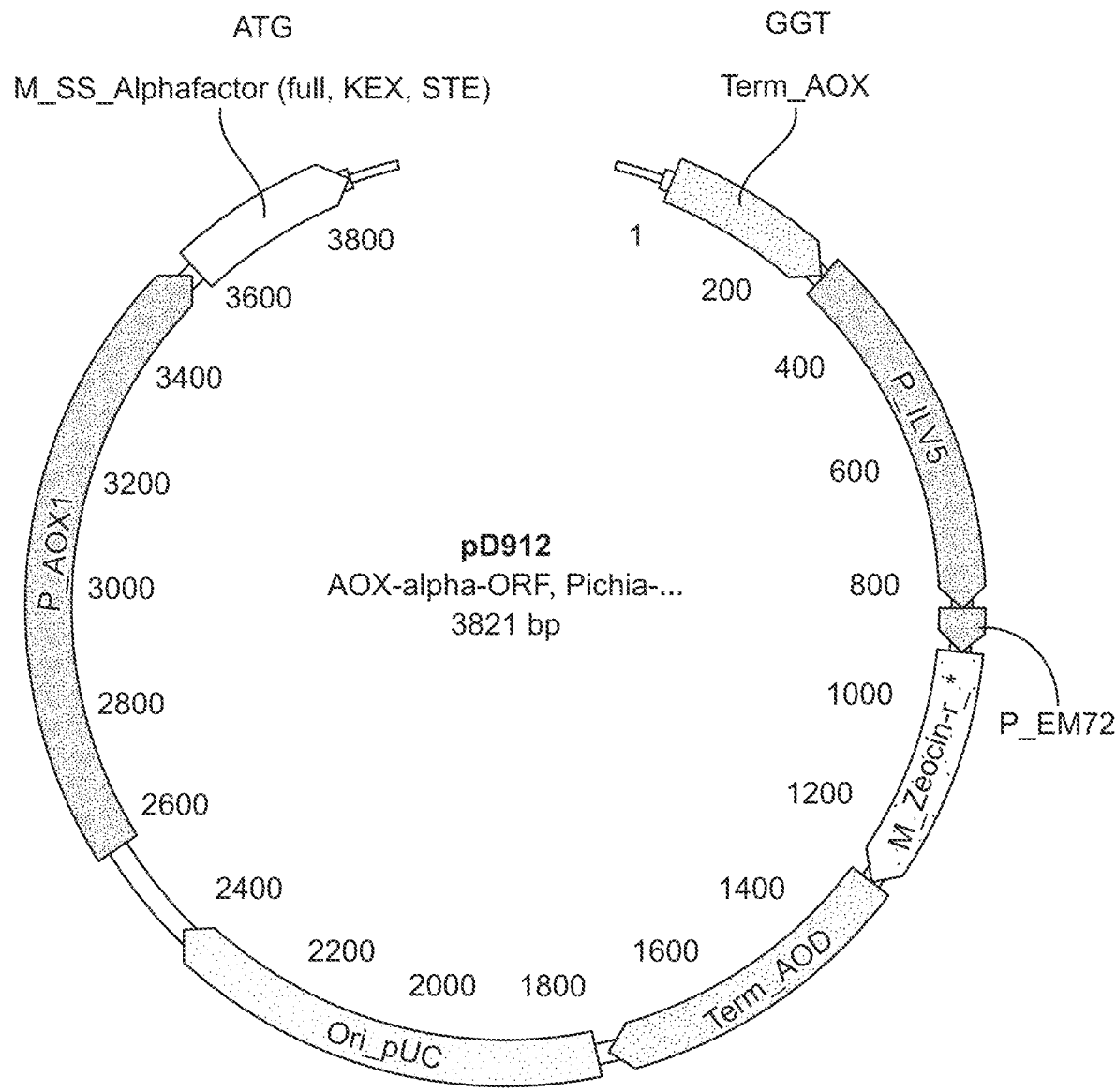
FIG. 1A shows a general map of the yeast expression vector pD912 (ATUM, formerly DNA 2.0) used to assemble plasmids used containing D1-1D2A-D12 and D1-GS-D12 fusion constructs.
Figure 1B:
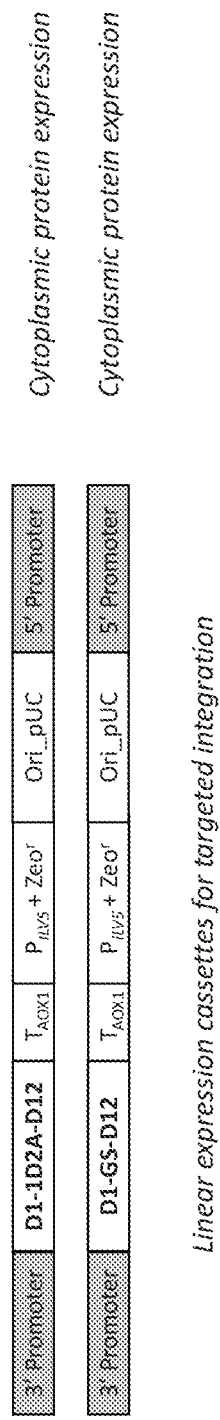
FIG. 1B shows a schematic of the linear integrative expression cassettes, which were prepared by PCR from the assembled plasmids as a DNA template. The assembled plasmids and linear cassettes had the following design: GAP or AOX1 promoter, followed by the amino-terminal His-tagged D1 and un-tagged D12 ORFs, fused with either 1D2A or GS linker (D1-1D2A-D12 and D1-GS-D12); AOX1 terminator sequence ($T_{AOX1}$); zeocin resistance gene under control of the ILV5 promoter ($P_{ILV5}$+$Zeo^r$); the sequence of the origin of replication (Ori_pUC); flanking sequences for the targeted integration (3' Promoter fragment contains the sequence of the actual promoter).

Aspects of the present disclosure can be further understood in light of the embodiments, section headings, figures, descriptions and examples, none of which should be construed as limiting the entire scope of the present disclosure in any way. Accordingly, the claims set forth below should be construed in view of the full breadth and spirit of the disclosure.

Each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

Unless otherwise defined, all technical and scientific terms used herein have the same meaning as commonly understood by one of ordinary skill in the art to which this disclosure belongs. Still, certain terms are defined herein with respect to embodiments of the disclosure and for the sake of clarity and ease of reference.

Sources of commonly understood terms and symbols may include: standard treatises and texts such as Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); Singleton, et al., Dictionary of Microbiology and Molecular biology, 2d ed., John Wiley and Sons, New York (1994), and Hale & Markham, the Harper Collins Dictionary of Biology, Harper Perennial, N.Y. (1991) and the like.

As used herein and in the appended claims, the singular forms "a" and "an" include plural referents unless the context clearly dictates otherwise. For example, the term "a protein" refers to one or more proteins, i.e., a single protein and multiple proteins. It is further noted that the claims can be drafted to exclude any optional element. As such, this statement is intended to serve as antecedent basis for use of such exclusive terminology as "solely," "only" and the like in connection with the recitation of claim elements or use of a "negative" limitation.

Numeric ranges are inclusive of the numbers defining the range. All numbers should be understood to encompass the midpoint of the integer above and below the integer i.e., the number 2 encompasses 1.5-2.5. The number 2.5 encompasses 2.45-2.55 etc. When sample numerical values are provided, each alone may represent an intermediate value in a range of values and together may represent the extremes of a range unless specified.

In the context of the present disclosure, "active" refers to catalytic activity. For example, an active vaccinia capping enzyme fusion has at least detectable RNA-triphosphatase activity, at least detectable RNA guanylyltransferase activity, and at least detectable RNA N7-guanine methyltransferase activity.

In the context of the present disclosure, "cap" refers to natural caps, such as $^7$mG, and to a compound of the general formula R3p$_3$N1-p-N(x), where R3 is a guanine, adenine, cytosine, uridine or analogs thereof (e.g., N$^7$-methylguanosine; m$^7$G), p$_3$ is a triphosphate linkage, N1 and Nx are ribonucleosides, x is 0-8 and p is, independently for each position, a phosphate group, a phosphorothioates, phosphorodithioate, alkylphosphonate, arylphosphonate, or a N-phosphoramidate linkage. Cap analogs are added at the 5' end of an RNA transcript in a process called co-transcriptional capping to yield a 5' capped RNA.

In the context of the present disclosure, "D1" and "D1 subunit" refer to the 97 kDa VCE subunit encoded by the vaccinia virus D1R gene (GeneID:3707562; UniProtKB ID: YP 232988.1) having RNA-triphosphatase, RNA guanylyltransferase and RNA N7-guanine methyltransferase enzymatic activities. D1 may have an amino acid sequence sharing at least 90%, at least 92%, at least 94%, at least 96%, or at least 98% identity with SEQ ID NO: 1. D1 optionally may comprise a histidine tag, for example, at its N-terminus. Unless otherwise indicated, D1 refers to the whole subunit. D1 optionally may comprise one or more modified amino acids (e.g., hydroxylated, phosphorylated, myristoylated, palmitoylated, isoprenylated, sulfated, ubiquitinated, glycosylated (e.g., N-linked, O-linked), lipoylated, acetylated, alkylated (e.g., methylated), biotinylated, amidated, oxidized (e.g., cysteines forming a S—S bond) or reduced).

In the context of the present disclosure, "D12" and "D12 subunit" refer to the 33 kDa VCE subunit encoded by the vaccinia virus D12L gene (GeneID:3707515; UniProtKB ID: YP 232999.1) and capable of enhancing the RNA N7-guanine methyltransferase activity of the D1 subunit (e.g., beyond such activity of D1 in the absence of D12). D12 may have an amino acid sequence sharing at least 90%, at least 92%, at least 94%, at least 96%, or at least 98% identity with SEQ ID NO: 1. Unless otherwise indicated, D12 refers to the whole subunit. D1 and D12 subunits may be associated with each other with or without a covalent linker. D12 optionally may comprise one or more modified amino acids (e.g., hydroxylated, phosphorylated, myristoylated, palmitoylated, isoprenylated, sulfated, ubiquitinated, glycosylated (e.g., N-linked, O-linked), lipoylated, acetylated, alkylated (e.g., methylated), biotinylated, amidated, oxidized (e.g., cysteines forming a S—S bond) or reduced).

In the context of the present disclosure, "expression system" refers to systems for producing a protein from a polynucleotide template comprising components to produce the protein according to an RNA template (e.g., enzymes, amino acids, an energy source), (optionally) components to produce the RNA template according to another RNA template or a DNA template (e.g., enzymes, nucleotides, an energy source). An expression system may comprise a bacterial (e.g., *Escherichia coli*) or yeast (e.g., *Kluyveromy-*

*ces lactis* or *Pichia pastoris*) expression system in which the protein is encoded by an RNA or DNA template within an expression cassette, a plasmid or other expression vector. An expression system may comprise a viral expression system in which the protein is encoded by an RNA or DNA template (e.g., in an expression cassette) within a viral genome or viral expression vector. Examples of cell-free expression systems may include or comprise cell extracts of *Escherichia coli* S30, rabbit reticulocytes or wheat germ; PURE-EXPRESS® (New England Biolabs, Ipswich, Mass.). An expression cassette may comprise, in some embodiments, an expression control sequence (e.g., promoter), a coding sequence encoding the gene product (e.g., protein) of interest (e.g., a vaccinia capping enzyme fusion), and/or one or more termination sequences (e.g., terminators). An expression control sequence (e.g., promoter) may comprise any promoter operative in a desired expression system, including, for example, a GAP promoter, an AOX1 promoter, a T7 promoter, a T5 promoter, a Ptac promoter, a Ptrc promoter, ParaBAD promoter, a PrhaBAD promoter, a Tet promoter or a PhoA phosphate-starvation promoter.

In the context of the present disclosure, "fusion" refers to two or more polypeptides, subunits, or proteins covalently joined to one another (e.g., by a peptide bond). For example, a protein fusion may refer to a non-naturally occurring polypeptide comprising the protein covalently joined to a reporter protein. Alternatively, where a protein comprises two separate polypeptide subunit chains, a fusion may comprise a non-naturally occurring combined polypeptide chain comprising the two subunits joined directly to each other by a peptide bond or through a peptide linker.

In the context of the present disclosure, "GS" refers to flexible linkers comprising glycine and serine, for example, repeats of glycine and serine residues $(Gly_xSer_y)_n$, where independently, x=1, 2, 3, 4, 5, 6, 7, 8, 9, 10, or more than 10, y=1, 2, 3, 4, 5, 6, 7, 8, 9, 10, or more than 10, and n=1, 2, 3, 4, 5, 6, 7, 8, 9, 10, or more than 10. For example, x, y, and/or n independently may be in a range of 1-3, 2-4, 3-5, 4-6, 5-7, 6-8, 7-9, 8-10, 9-11, 10-12, or more.

In the context of the present disclosure, "1D2A" refers to a polypeptide comprising, in an N-terminal to C-terminal direction, 14 amino acid residues of the capsid protein 1D, and a 2A proteinase of picornaviruses including, for example, 2A proteinases of rhinoviruses. An 1D2A may comprise a 2A proteinase derived from foot and mouth disease virus.

In the context of the present disclosure, "peptide linker" refers to a peptide, oligopeptide, polypeptide chain comprising two or more (e.g., 2-25, 20-40, 5-50, 10-100, >100) amino acids adapted to form a link (e.g., via peptide bonds at the N-terminal and C-terminal ends of the linker) between subunits of vaccinia capping enzyme. A peptide linker may comprise one or more modified amino acids (e.g., hydroxylated, phosphorylated, myristoylated, palmitoylated, isoprenylated, sulfated, ubiquitinated, glycosylated (e.g., N-linked, O-linked), lipoylated, acetylated, alkylated (e.g., methylated), biotinylated, amidated, oxidized (e.g., cysteines forming a S—S bond) or reduced). Examples of peptide linkers include GS and 1D2A.

In the context of the present disclosure, "non-naturally occurring" refers to a polynucleotide, polypeptide, carbohydrate, lipid, or composition that does not exist in nature. Such a polynucleotide, polypeptide, carbohydrate, lipid, or composition may differ from naturally occurring polynucleotides polypeptides, carbohydrates, lipids, or compositions in one or more respects. For example, a polymer (e.g., a polynucleotide, polypeptide, or carbohydrate) may differ in the kind and arrangement of the component building blocks (e.g., nucleotide sequence, amino acid sequence, or sugar molecules). A polymer may differ from a naturally occurring polymer with respect to the molecule(s) to which it is linked. For example, a "non-naturally occurring" protein may differ from naturally occurring proteins in its secondary, tertiary, or quaternary structure, by having a chemical bond (e.g., a covalent bond including a peptide bond, a phosphate bond, a disulfide bond, an ester bond, and ether bond, and others) to a polypeptide (e.g., a fusion protein), a lipid, a carbohydrate, or any other molecule. Similarly, a "non-naturally occurring" polynucleotide or nucleic acid may contain one or more other modifications (e.g., an added label or other moiety) to the 5'-end, the 3' end, and/or between the 5'- and 3'-ends (e.g., methylation) of the nucleic acid. A "non-naturally occurring" composition may differ from naturally occurring compositions in one or more of the following respects: (a) having components that are not combined in nature, (b) having components in concentrations not found in nature, (c) omitting one or components otherwise found in naturally occurring compositions, (d) having a form not found in nature, e.g., dried, freeze dried, crystalline, aqueous, and (e) having one or more additional components beyond those found in nature (e.g., buffering agents, a detergent, a dye, a solvent or a preservative). All publications, patents, and patent applications cited, listed, or otherwise mentioned in this specification are herein incorporated by reference to the same extent as if each individual publication, patent, or patent application was specifically and individually indicated to be incorporated by reference.

In the context of the present disclosure, "polynucleotide linker sequence" refers to a polynucleotide sequence that links the 3' end of one subject polynucleotides to the 5' end of another polynucleotide. A polynucleotide linker sequence may encode a polypeptide linker (e.g., a GS linker) and/or may allow, cause or promote ribosome skipping during translation.

In the context of the present disclosure, "transcript" refers to a polynucleotide template for a polypeptide. A transcript may comprise RNA (e.g., ssRNA), a cap or cap analog, and/or a polyA tail. A transcript may be capable of translation in a cell (e.g., a bacterial cell and/or a yeast cell). For example, a transcript may be or comprise mRNA. A fusion transcript may comprise polynucleotide templates for two or more polypeptides in a single polynucleotide.

The potential for mRNA vaccines to transform the treatment of infectious diseases has gained considerable traction since it was first proposed. Manufacturing may be cell-free and scalable. Once the sequence of a desired immunogen is provided, the time required to produce clinical batches of vaccine might be weeks instead of months. Such rapid production may limit or even avert widespread outbreaks.

Production of stable mRNA capable of efficient translation upon introduction to a subject may require an appropriate cap structure. Vaccinia virus, like most viruses, has a robust set of tools to co-opt host cell machinery for the production of viral proteins. One such tool is the vaccinia capping enzyme, which forms a Cap 0 structure (m7Gppp5'N) at the 5' end of uncapped RNA molecules through its RNA triphosphatase, guanylyltransferase, and guanine methyltransferase activities. In cells, capping viral transcripts allows them to be transcribed by the infected cells. Other transcripts may be capped rapidly in vitro in the presence of the vaccinia capping enzyme, reaction buffer, GTP, and the methyl donor, SAM. Capping by VCE may be nearly 100% efficient and all capped structures may be added in the proper orientation (e.g., compared to co-transcriptional addition of some cap analogs). Capping by vaccinia capping enzyme may be desired or even required for production of an effective RNA vaccine. For example, a suitable cap structure may impact the stability and translatability of an RNA vaccine.

Production of active vaccinia capping enzyme for cell-free vaccine production can be challenging. Properties of VCE may impede production (e.g., high capacity production) and use of the enzyme. For example, efforts to express the vaccinia virus D1R gene in bacteria and yeast as a means to produce and recover the 97 kDa subunit result in low yields. Without limiting any embodiment to any specific mechanism of action, this appears to be due, at least in part, to the insolubility and/or hydrophobicity of the 97 kDa subunit. In addition, in vitro assembly of the small and large subunits into a heterodimer may yield an enzyme with little to no catalytic activity. Separately produced subunits may not be present in an appropriate ratio or conformation to efficiently or productively bind to one another and/or bind to substrates.

A 2A sequence derived from foot-and-mouth disease virus can be used as an alternative strategy to generate different proteins derived from a fusion protein precursor (Osborn et al. 2005). A region of 18 amino acid residues from 2A followed by a proline promoted "cleavage" in a co-translational manner using a nonproteolytic mechanism termed "ribosome skipping" (Donnelly, Luke et al. 2001). Addition of 14 amino acid residues of the capsid protein 1D to the N-terminal of 2A increased the activity of self-processing up to 99% (Donnelly, Hughes et al. 2001). An artificial polyprotein precursor comprising this 1D2A sequence flanked by reporter genes was efficiently processed into separate polypeptides in tested eukaryotic cells, including *Pichia pastoris* (Lee et al. 2012; Rasala et al. 2012; Chng et al. 2015; Sun et al. 2012; de Amorim Araújo et al. 2015). After processing, the 1D2A peptide remains as a C-terminal extension of the upstream protein and all products downstream of 2A contain a proline residue at the N-terminal (Ryan et al. 1991; Donnelly, Luke et al. 2001; De Felipe et al. 2003).

Linkers used in the construction of multidomain proteins may comprise repeats of glycine and serine residues $(Gly_xSer_y)_n$. The combination of flexible (Gly) and hydrophilic (Ser) residues in these linkers has multiple advantages, since it may not interfere with a folding and function of the fusion proteins. The absence of protease-sensitive sites of the common eukaryotic proteases in the Gly-Ser linker sequences potentially contributes to the stability of the linker of the chimeric proteins (Crasto and Feng 2000).

The present disclosure relates to compositions, methods, and kits for producing active vaccinia capping enzyme. For example, compositions may comprise a vaccinia capping enzyme fusion comprising (e.g., in a single polypeptide chain) a D1 subunit, a D12 subunit, and a linker (e.g., a flexible linker, a cleavable linker) positioned between the carboxy terminal end of the D1 subunit and the amino terminal end of the D12 subunit. A vaccinia capping enzyme fusion may comprise, for example, in an N-terminal to C-terminal direction, (a) a polypeptide having a sequence at least 90% identical to positions 24 to 867 of SEQ ID NO:1, (b) a linker having at least 90% identity to SEQ ID NO: 3 or at least 90% identity to SEQ ID NO: 5, and (c) a polypeptide having a sequence at least 90% identity to SEQ ID NO: 2. For example, a composition may comprise a vaccinia capping enzyme fusion comprising a polypeptide having an amino acid sequence at least 90% (e.g., at least 92%, at least 95%, at least 97%) identical to SEQ ID NO: 4 or at least 90% (e.g., at least 92%, at least 95%, at least 97%) identical to SEQ ID NO: 6 or at least 90% (e.g., at least 92%, at least 95%, at least 97%) identical to SEQ ID NO: 8. A vaccinia capping enzyme fusion may be stable as a single polypeptide chain and/or may have a desired susceptibility to cleavage (e.g., by a protease at a location in or near the linker).

Compositions may comprise, in some embodiments, a vaccinia capping enzyme fusion transcript (e.g., a single polynucleotide chain) comprising a sequence encoding a vaccinia capping enzyme fusion. For example, a vaccinia capping enzyme fusion transcript may comprise, in a 5' to 3' direction: (a) a sequence encoding a D1 subunit, (b) a linker (e.g., an 1D2A linker, a sequence encoding a flexible linker or a cleavable linker), and (c) a sequence encoding a D12 subunit. For example, a composition may comprise a vaccinia capping enzyme fusion transcript may encode a polypeptide having an amino acid sequence at least 90% identical to SEQ ID NO: 4 or at least 90% identical to SEQ ID NO: 6 or at least 90% identical to SEQ ID NO: 8. A vaccinia capping enzyme fusion transcript, according to some embodiments, may comprise a cap (e.g., a 5' Cap 0). Compositions optionally may comprise one or more of the components set forth below for kits. In some embodiments, a composition may be glycerol-free, may be dry (e.g., as a result of lyophilization), and/or may be aqueous.

Methods for production of vaccinia capping enzyme may comprise, for example, contacting a vaccinia capping enzyme fusion polynucleotide comprising, in a 5' to 3' orientation, (a) a sequence encoding a polypeptide having at least 90% identity to D1, (b) a sequence encoding a linker having at 90% identity to 1D2A (SEQ ID NO: 3) or at least 90% identity to GS (SEQ ID NO: 5), and (c) at least 90% identity to D12, with an expression system (e.g., a bacterial expression system, a yeast expression system, a viral expression system or a cell-free expression system). A method may optionally comprise capping a vaccinia capping enzyme fusion polynucleotide with a cap or a cap analog.

Kits

The present disclosure further relates to kits including a vaccinia capping enzyme fusion. For example, a kit may include a vaccinia capping enzyme fusion and an uncapped ribonucleic acid, dNTPs, rNTPs, primers, other enzymes (e.g., decapping enzymes, polymerases, other enzymes, or both), buffering agents, or combinations thereof. A vaccinia capping enzyme fusion may be included in a storage buffer (e.g., comprising glycerol and a buffering agent). A kit may include a reaction buffer which may be in concentrated form, and the buffer may contain additives (e.g. glycerol), salt (e.g. KCl), reducing agent, EDTA or detergents, among others. A kit comprising dNTPs may include one, two, three or all four of dATP, dTTP, dGTP and dCTP. A kit comprising rNTPs may include one, two, three of all four or rATP, rUTP, rGTP and rCTP. A kit may further comprise one or more modified nucleotides. A kit may optionally comprise one or more primers (random primers, bump primers, exonuclease-resistant primers, chemically-modified primers, custom sequence primers, or combinations thereof). One or more components of a kit may be included in one container for a single step reaction, or one or more components may be contained in one container, but separated from other components for sequential use or parallel use. The contents of a kit may be formulated for use in a desired method or process.

A kit is provided that contains: (i) A vaccinia capping enzyme fusion; and (ii) a buffer. A vaccinia capping enzyme fusion may have a lyophilized form or may be included in a buffer (e.g., a storage buffer or a reaction buffer in concentrated form). A kit may contain a vaccinia capping enzyme fusion in a mastermix suitable for receiving and capping a template ribonucleic acid. A vaccinia capping enzyme fusion may be a purified enzyme so as to contain no other detectable enzyme activities. The reaction buffer in (ii) and/or storage buffers containing a vaccinia capping enzyme fusion in (i) may include non-ionic, ionic e.g. anionic or zwitterionic surfactants, denaturants, and/or crowding agents. A kit may include a vaccinia capping enzyme fusion and the reaction buffer in a single tube or in different tubes.

A subject kit may further include instructions for using the components of the kit to practice a desired method. The instructions may be recorded on a suitable recording medium. For example, instructions may be printed on a substrate, such as paper or plastic, etc. As such, the instructions may be present in the kits as a package insert, in the labeling of the container of the kit or components thereof (i.e., associated with the packaging or sub-packaging) etc. Instructions may be present as an electronic storage data file residing on a suitable computer readable storage medium (e.g., a CD-ROM, a flash drive). Instructions may be provided remotely using, for example, cloud or internet resources with a link or other access instructions provided in or with a kit.

EXAMPLES

Some specific embodiments may be illustrated by one or more of the examples provided herein.

Example 1: Expression of 2A Fusion Construct Produces Active Heterodimeric VCE A. Plasmids and Linear Expression Cassettes The pD912(GAP)/D1-1D2A-D12 plasmid comprises sequences encoding vaccinia mRNA capping enzyme D1 and D12 subunits, arranged to be expressible as a single polypeptide. A sequence encoding a D1 subunit having an amino-terminal His-tag (SEQ ID NO:1) was fused to a sequence encoding the amino-terminus of the un-tagged D12 subunit (SEQ ID NO:2) via a sequence encoding a 33 amino acid residue 1D2A linker (SEQ ID NO:3).

The plasmid was synthesized and assembled using PCR and in vitro DNA assembly methods. The pD912(GAP) was prepared from pD912(AOX) vector by replacing 462 bp long AOX1 promoter sequence with 483 bp long DNA fragment containing *Pichia pastoris* GAP promoter. The pD912(GAP) vector backbone without the sequence encoding for secretion leader was amplified by PCR. The ORFs of D1 and D12 were amplified from pET23bVCE plasmid using PCR method. All amplified DNA fragments were purified by gel extraction and assembled into the plasmid using NEBuilder HiFi DNA Assembly Mix. The resulting pD912(GAP)/D1-1D2A-D12 plasmid contained the self-processive D1-1D2A-D12 construct under control of the constitutive GAP promoter for the cytoplasmic expression in *Pichia pastoris*. The non-naturally occurring VCE protein sequence encoded by pD912(GAP)/D1-1D2A-D12 plasmid corresponds to SEQ ID NO:4.

Another variant of a heterodimeric D1-1D2A-D12 fusion was generated by assembling a construct into the pD912 (AOX) vector. The resulting pD912(AOX1)/D1-1D2A-D12 plasmid contained a fusion construct under control of the methanol inducible AOX1 promoter for the cytoplasmic expression in *Pichia pastoris*.

Another active heterodimeric construct of vaccinia mRNA capping enzyme subunits was generated by fusion of D1 and D12 via flexible non-cleavable linker (Gly-Gly-Gly-Gly-Ser)$_3$ SEQ ID NO:5. The genes of D1 and D12 were amplified from pET23bVCE plasmid using PCR method. The pD912(GAP) vector backbone minus the sequence encoding for secretion leader was amplified by PCR. All amplified DNA fragments were purified by gel extraction and assembled into the plasmid using NEBuilder HiFi DNA Assembly Mix. The resulting pD912(GAP)/D1-GS-D12 plasmid contained D1-GS-D12 construct under control of the constitutive GAP promoter for the cytoplasmic expression in *Pichia pastoris*. The protein sequence encoded by pD912(GAP)/D1-GS-D12 plasmid corresponds to SEQ ID NO:6.

A linear expression cassette was PCR amplified from the assembled plasmids (FIG. 1A). The amplified expression cassette was purified by gel extraction and used for yeast transformation.

B. Yeast Transformation and Integration

*Pichia pastoris* aox1Δ (MutS) (ATUM, formerly DNA 2.0) strain was used in all experiments under this Example. *Pichia pastoris* electrocompetent cells were prepared by a lithium acetate/DTT method (Wu and Letchworth, 2004). 0.2 μg of a purified linear expression cassette was introduced into *Pichia pastoris* electrocompetent cells (electroporation conditions: 1.5 KV, 25 μF and 200 Ohm; 0.2 mm cuvette) followed by selection of transformants by growth on yeast peptone dextrose (YPD) agar medium supplemented with 1 M sorbitol and 500 μg/mL Zeocin (Teknova) for 3-4 days at 30° C.

For the identification of transformants by PCR, genomic DNA was isolated from each colony selected for testing using a lithium acetate/sodium dodecyl sulfate (LiOAc/SDS) method (Looke et al., 2011). PCR was used to identify transformants having an integrated expression cassette. The amplified genomic DNA fragments were purified and used to verify the sequence of the integrated construct.

C. Yeast Culture Conditions and Expression

For constructs containing GAP promoter, *Pichia pastoris* transformants were grown at 30° C. in 5-25 mL of yeast medium (1% yeast extract, 2% peptone, 1.34% yeast nitrogen base (YNB) without amino acids, 0.0004% biotin, 10 mM potassium phosphate, pH 6.0) supplemented with 2% glycerol as the carbon source. After 48 hours, the cells and spent culture media were harvested.

For constructs containing AOX1 promoter, *Pichia pastoris* transformants were grown to near saturation (OD=20 at 600 nm) at 30° C. in 10 mL of yeast medium (1% yeast extract, 2% peptone, 1.34% yeast nitrogen base, 0.0004% biotin, 10 mM potassium phosphate, pH 6.0) supplemented with 1% glycerol as the carbon source. Cells were harvested and resuspended in 4 ml of the same medium with 0.5% (v/v) methanol instead of glycerol and incubated for 48 hours.

D. Protein Purification and Analysis

To prepare cell lysate, cells were resuspended in 20 mM Tris-HCl, pH7.5 buffer, containing 100 mM NaCl. The cells disrupted using a high pressure homogenizer at 30 KPsi (Dyhydromatics), and the cell lysate pre-cleared by centrifugation at 17000×g for 45 minutes. The cell lysates and spent culture media were analyzed by SDS-PAGE on 10-20% polyacrylamide gel, followed by western blotting with His-tag antibodies (Thermofisher) or mouse monoclonal antibodies against D1 or D12 subunits (GenScript).

Purification of the expressed recombinant fusion proteins from cell lysates was performed using the NEBExpress Ni Spin columns according to manufacturer's recommendations (NEB).

E. In Vitro mRNA Capping Assay

In vitro capping reactions were carried out in a 10 µL reaction containing 1× capping buffer (50 mM Tris pH 8.0, 5 mM KCl, 1 mM $MgCl_2$, 1 mM DTT) supplemented with 0.1 mM S-adenosylmethionine, 0.5 mM GTP, 500 nM substrate RNA (5'-pppGUAGAACUUCGUCGAGUACG-CUCAA[FAM]-3' (SEQ ID NO:7), Bio-Synthesis, Inc.), and purified enzyme at 37° C. for 30 minutes. Reactions were stopped by adding 10 µL of quenching solution (20 mM EDTA, 2% SDS). Reactions were diluted in nuclease-free water to reach a final substrate concentration of 5 nM before capillary electrophoresis on either an Applied Biosystems 3130xl Genetic Analyzer (16 capillary array) or an Applied Biosystems 3730xl Genetic Analyzer (96 capillary array) using GeneScan 120 LIZ dye Size Standard (Applied Biosystems). Reaction products were analyzed using PeakScanner software (Thermo Fisher Scientific).

F. Results: Active Enzyme was Produced

Western blot analysis of the transformants expressing cytoplasmic heterodimer D1-1D2A-D12 indicated that the recombinant fusion protein is expressed in *Pichia pastoris* cytoplasm as a soluble protein. The results indicate, that the self-processive D1-1D2A-D12 is only partially processed, since D1 and D12 subunits were present in both fused and individual forms (FIG. 2).

Figure 2:
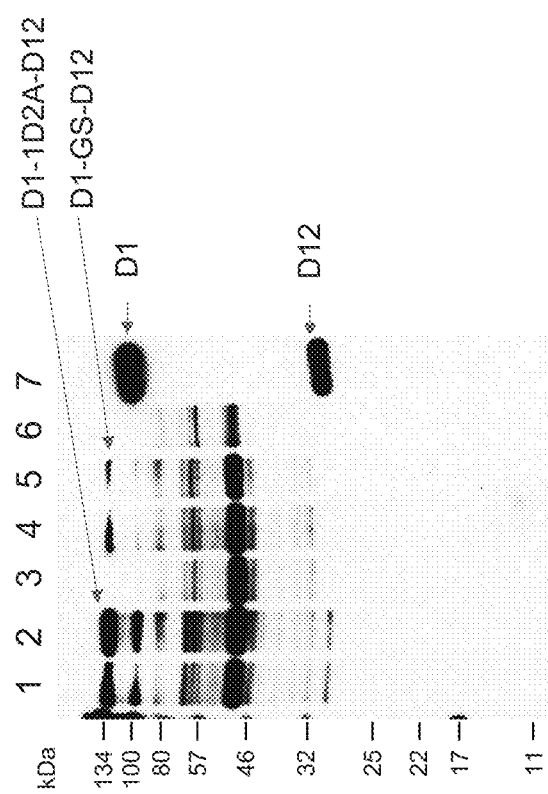
FIG. 2 shows the cytoplasmic expression of the D1-1D2A-D12 and D1-GS-D12 fusion proteins in *Pichia pastoris* cells transformed with constructs containing GAP promoter. The transformants were grown in the medium with 2% glycerol at 30° C. The cells were harvested after 48 hours incubation. The cell lysates were prepared by high pressure homogenization and analyzed by analyzed by SDS-PAGE on 10-20% polyacrylamide gel, followed by western blotting with His-tag antibodies and mouse monoclonal antibodies against D12 subunit. Lanes 1, 2—cell lysates of *Pichia* transformants #1 and #2 expressing D1-1D2A-D12; lanes 3, 6—control *Pichia* cell lysates; lanes 4, 5—cell lysates of *Pichia* transformants #1 and #2 expressing D1-GS-D12; lane 7—recombinant VCE (NEB).
Figure 3:
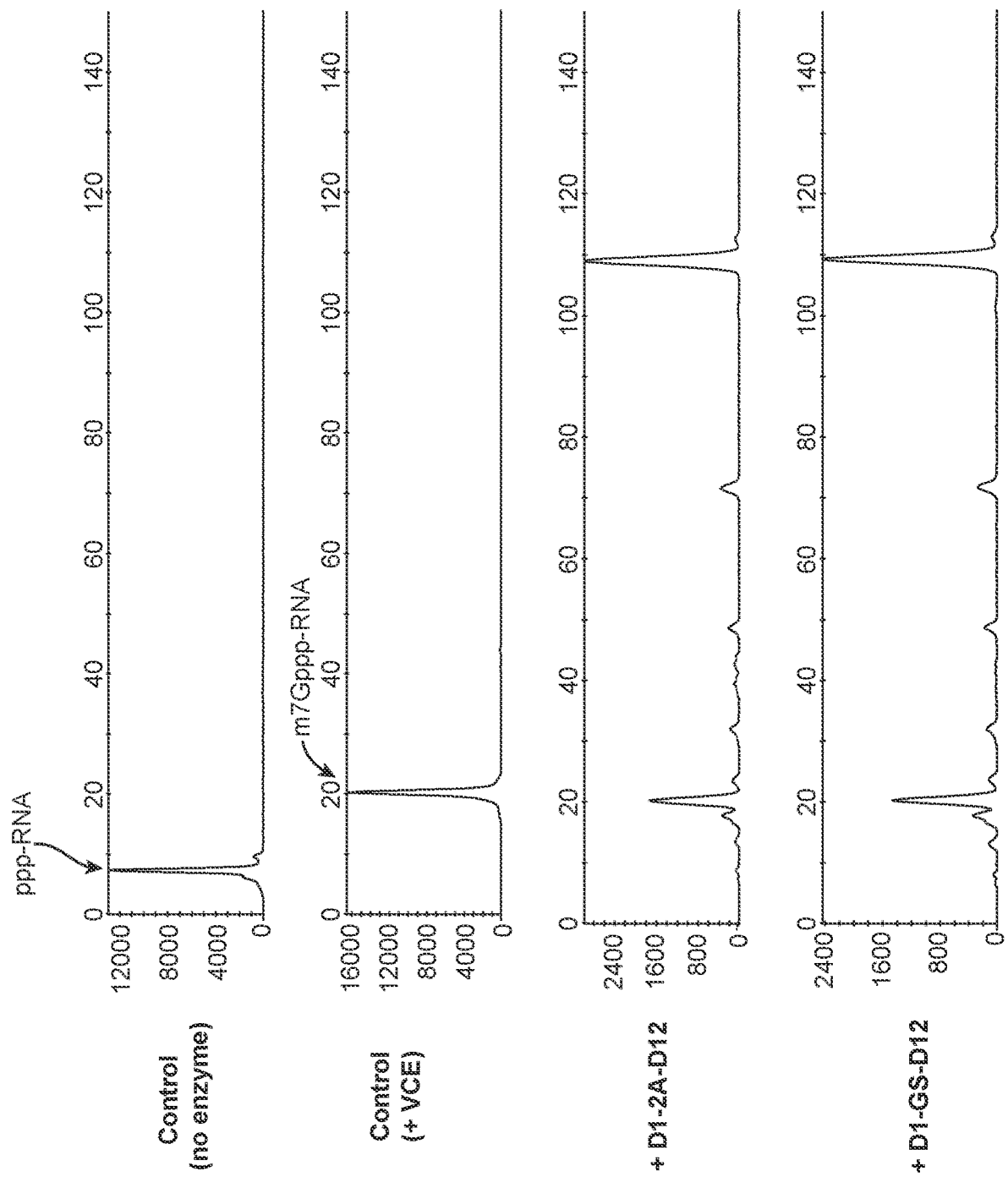
FIG. 3 shows the activity of the partially purified D1-1D2A-D12 and D1-GS-D12 proteins. The recombinant fusion proteins were purified from the cell lysates using the NEBExpress nickel spin columns. The activity of the purified proteins was assayed using an in vitro mRNA capping assay as described in Example 1E.

The cytoplasmic heterodimer D1-GS-D12 fusion protein containing flexible linker is also expressed as a single polypeptide (FIG. 2). Partially purified D1-1D2A-D12 and D1-GS-D12 were tested for mRNA capping activity. Both recombinant proteins were active (FIG. 3).

REFERENCES

Cong, P. and S. Shuman (1993). "Covalent catalysis in nucleotidyl transfer. A KTDG motif essential for enzyme-GMP complex formation by mRNA capping enzyme is conserved at the active sites of RNA and DNA ligases." *J Biol Chem* 268(10): 7256-60.

Niles, E. G. and L. Christen (1993). "Identification of the vaccinia virus mRNA guanyltransferase active site lysine." *J Biol Chem* 268(33): 24986-9.

Higman, M. A. and E. G. Niles (1994). "Location of the S-adenosyl-L-methionine binding region of the vaccinia virus mRNA (guanine-7-)methyltransferase." *J Biol Chem* 269(21): 14982-7.

Mao, X. and S. Shuman (1994). "Intrinsic RNA (guanine-7) methyltransferase activity of the vaccinia virus capping enzyme D1 subunit is stimulated by the D12 subunit. Identification of amino acid residues in the D1 protein required for subunit association and methyl group transfer." *J Biol Chem* 269(39): 24472-9.

Gong, C. and S. Shuman (2003). "Mapping the active site of vaccinia virus RNA triphosphatase." *Virology* 309(1): 125-34.

Higman, M. A., N. Bourgeois, et al. (1992). "The vaccinia virus mRNA (guanine-N-7-)-methyltransferase requires both subunits of the mRNA capping enzyme for activity." *J Biol Chem* 267(23): 16430-7.

Higman, M. A., L. A. Christen, et al. (1994). "The mRNA (guanine-7) methyltransferase domain of the vaccinia virus mRNA capping enzyme. Expression in *Escherichia coli* and structural and kinetic comparison to the intact capping enzyme." *J Biol Chem* 269(21): 14974-81.

Osborn M J, Panoskaltsis-Mortari A, Mcelmurry R T, Bell S K, Vignali D A A, Ryan M D, Wilber A C, McIvor R S, Tolar J, Blazar B R. A picornaviral 2A-like sequence-based tricistronic vector allowing for high-level therapeutic gene expression coupled to a dual-reporter system. Mol Ther. 2005; 12:569-574.

Donnelly M L L, Luke G, Mehrotra A, Li X, Hughes L E, Gani D, Ryan M D. b Analysis of the aphthovirus 2A/2B polyprotein 'cleavage' mechanism indicates not a proteolytic reaction, but a novel translational effect: a putative ribosomal 'skip' J Gen Virol. 2001; 82:1013-1025.

Donnelly M L L, Hughes L E, Luke G, Mendoza H, ten Dam E, Gani D, Ryan M D. The 'cleavage' activities of foot-and-mouth disease virus 2A site-directed mutants and naturally occurring '2A-like' sequences. J Gen Virol. 2001; 82:1027-1041. doi: 10.1099/0022-1317-82-5-1027.

Lee D S, Lee K H, Jung S, Jo E J, Han K H, Bae H J. Synergistic effects of 2A-mediated polyproteins on the production of lignocellulose degradation enzymes in tobacco plants. J Exp Bot. 2012; 63:4797-4810.

Rasala B A, Lee P A, Shen Z, Briggs S P, Mendez M, Mayfield S P. (2012). Robust expression and secretion of Xylanase1 in *Chlamydomonas reinhardtii* by fusion to a selection gene and processing with the FMDV 2A peptide. PLoS One. 7:e43349.

Chng J, Wang T, Nian R, Lau A, Hoi K M, Ho S C, Gagnon P, Bi X, Yang Y. (2015). Cleavage efficient 2A peptides for high level monoclonal antibody expression in CHO cells. MAbs. 7:403-412.

Sun Y F, Lin Y, Zhang J H, Zheng S P, Ye Y R, Liang X X, Han S Y. (2012). Double *Candida antarctica* lipase B co-display on *Pichia pastoris* cell surface based on a self-processing foot-and-mouth disease virus 2A peptide. Appl Microbiol Biotechnol. 96:1539-1550.

de Amorim Araújo, J., Ferreira, T. C., Rubini, M. R., Duran, A. G., De Marco, J. L., de Moraes, L. M., & Torres, F. A. (2015). Coexpression of cellulases in *Pichia pastoris* as a self-processing protein fusion. *AMB Express*, 5(1), 84.

Ryan M D, King A M Q, Thomas G P. (1991). Cleavage of foot-and-mouth disease virus polyprotein is mediated by residues located within a 19 amino acid sequence. *J Gen Virol.* 72:2727-2732.

De Felipe P, Hughes L E, Ryan M D, Brown J D. (2003). Co-translational, intraribosomal cleavage of polypeptides by the foot-and-mouth disease virus 2A peptide. J Chem. 278:11441-11448.

Crasto, C. J., & Feng, J. A. (2000). LINKER: a program to generate linker sequences for fusion proteins. *Protein engineering*, 13(5), 309-312.

Wu, S., & Letchworth, G. J. (2004). High efficiency transformation by electroporation of *Pichia pastoris* pretreated with lithium acetate and dithiothreitol. *BioTechniques*, 36(1), 152-154.

Lõoke, M., Kristjuhan, K., & Kristjuhan, A. (2011). Extraction of genomic DNA from yeasts for PCR-based applications. *BioTechniques*, 50(5), 325-328.

What is claimed is:

1. A composition comprising a vaccinia capping enzyme fusion, wherein the vaccinia capping enzyme fusion comprises, in an N-terminal to C-terminal orientation:
   (a) a D1 subunit;
   (b) a linker; and
   (c) a D12 subunit,
   wherein the linker has at least 90% identity to SEQ ID NO: 3.

2. A composition according to claim 1, wherein the D1 subunit has an amino acid sequence having at least 90% identity to positions 24 to 867 of SEQ ID NO: 1.

3. A composition according to claim 1, wherein the D1 subunit has an amino acid sequence having at least 90% identity to SEQ ID NO: 1.

4. A composition according to claim 1, wherein the D 12 subunit has an amino acid sequence having at least 90% identity to SEQ ID NO: 2.

5. A cell comprising the composition according to claim 1.

6. A cell according to claim 5, wherein the vaccinia capping enzyme fusion protein has an amino acid sequence at least 90% identical to SEQ ID NO: 4 or at least 90% identical to SEQ ID NO: 6 or at least 90% identical to SEQ ID NO: 8.

7. A cell according to claim 5, wherein the cell is a *Kluyveromyces lactis* cell or a *Pichia pastoris* cell.

8. A vaccinia capping enzyme fusion, comprising in an N-terminal to C-terminal orientation: (a) a D1 subunit; (b) a linker; and (c) a D12 subunit, wherein the linker has ° at least 90% identity to SEQ ID NO: 3.

* * * * *